(12) United States Patent
Boersma et al.

(10) Patent No.: US 8,831,388 B2
(45) Date of Patent: Sep. 9, 2014

(54) COATED WAVEGUIDE FOR OPTICAL DETECTION

(75) Inventors: Arjen Boersma, 's-Hertogenbosch (NL); Tatiana Johanna Judith Teerling, Pijnacker (NL); Theodorus Henricus Cornelus Panken, Eindhoven (NL); Lun Kai Cheng, Krimpen a/d Ijssel (NL)

(73) Assignee: Nederlandse Organisate voor Toegepast-Natuurwetenschappelijk Onderzoek TNO, Delft (NL)

( * ) Notice: Subject to any disclaimer, the term of this patent is extended or adjusted under 35 U.S.C. 154(b) by 1002 days.

(21) Appl. No.: 12/809,391

(22) PCT Filed: Dec. 19, 2008

(86) PCT No.: PCT/NL2008/050823
§ 371 (c)(1),
(2), (4) Date: Nov. 24, 2010

(87) PCT Pub. No.: WO2009/082213
PCT Pub. Date: Jul. 2, 2009

(65) Prior Publication Data
US 2011/0200285 A1 Aug. 18, 2011

(30) Foreign Application Priority Data
Dec. 20, 2007 (EP) .................................. 07150214

(51) Int. Cl.
*G02B 6/34* (2006.01)
*G02B 6/00* (2006.01)
*G01N 21/77* (2006.01)

(52) U.S. Cl.
CPC ..................... *G01N 21/774* (2013.01)
USPC ............................................. 385/37; 385/147

(58) Field of Classification Search
None
See application file for complete search history.

(56) References Cited

U.S. PATENT DOCUMENTS

| | | | |
|---|---|---|---|
| 5,773,486 A | 6/1998 | Chandross et al. | |
| 6,204,304 B1* | 3/2001 | Houlihan et al. | 522/88 |
| 6,396,983 B1* | 5/2002 | Atkins et al. | 385/37 |
| 6,603,901 B1* | 8/2003 | Hale et al. | 385/37 |
| 7,058,249 B2* | 6/2006 | Purchase et al. | 385/14 |
| 2002/0009274 A1* | 1/2002 | Gharavi | 385/122 |
| 2004/0184733 A1* | 9/2004 | Starodubov | 385/37 |

(Continued)

FOREIGN PATENT DOCUMENTS

| | | |
|---|---|---|
| CN | ZL 200880127066.X | 12/2013 |
| EP | 0677738 A | 10/1995 |
| JP | 2000206378 | 7/2000 |

OTHER PUBLICATIONS

Liu, X. et al., Demonstration of etched cladding fiber Bragg grating-based sensors with hydrogel coating, Sensors and Actuators B 96:468-472, 2003.

(Continued)

*Primary Examiner* — Tina Wong
(74) *Attorney, Agent, or Firm* — Lucas & Mercanti, LLP

(57) ABSTRACT

The invention relates to a waveguide, comprising a grating in at least a part of the waveguide, which waveguide comprises a coating, the coating comprising a polymer, which polymer comprises an aliphatic chain, which aliphatic chain is provided with hydrophilic side-chains. The invention further relates to a sensor system comprising a waveguide according to any one of the preceding claims, a light source, and a photo-detector.

23 Claims, 1 Drawing Sheet

Reproducibility of the manufacturing process and the sensor response for four fibres and four cycli

(56) References Cited

U.S. PATENT DOCUMENTS

| | | | |
|---|---|---|---|
| 2005/0129360 A1* | 6/2005 | Andre et al. | 385/37 |
| 2005/0276541 A1* | 12/2005 | Girardon et al. | 385/37 |
| 2006/0133756 A1* | 6/2006 | Shelnut et al. | 385/129 |
| 2006/0133766 A1* | 6/2006 | Shelnut et al. | 385/147 |

OTHER PUBLICATIONS

European Search Report issued in European Patent Application No. 07150214 and dated Mar. 17, 2008.

Yeo et al.: "Characterisation of a polymer-coated fibre Bragg grating sensor for relative humidity sensing" Sensors and Actuators B, Elsevier Sequoia S.A., Lausanne, CH vol. 110, No. 1, Sep. 30, 2005 pp. 148-156 XP005003710, ISSN: 0925-4005.

Patrick Boland et al.: "Fiber Bragg grating multi-chemical sensor" Proceedings of the SPIE vol. 6371, 2006 pp. 637191-1-637109-11 XP002513103.

Cong J et al.: "Fiber optic Bragg grating sensor based on hydrogels for measuring salinity" Sensors and Actuators B, Elsevier Sequoia S.A., Lausanne, CH vol. 87, No. 3, Dec. 20, 2002 pp. 487-490 XP004393693, ISSN: 0925-4005.

Yeo T L et al.: "Technical Note; Demonstration of a fibre-optic sensing technique for the measurement of moisture absorption in concrete" Smart Materials and Structures, IOP Publishing Ltd., Bristol, GB vol. 15, No. 2, Apr. 1, 2006 pp. N40-N45, XP020105396, ISSN: 0964-1726.

Grattan K T V et al.: "Polymer-Coated Fiber Bragg Grating for Relative Humidity Sensing" IEEE Sensors Journal, IEEE Service Center, New York, NY, US vol. 5, No. 5, Oct. 1, 2005 pp. 1082-1089 XP011138571, ISSN: 1530-437X.

Battiston F M et al.: "A chemical sensor based on a microfabricated cantilever array with simultaneous resonance-frequency and bending readout" Sensors and Actuators B, Elsevier Sequoia S.A., Lausanne, CH vol. 77, No. 1-2, Jun. 15, 2001 pp. 122-131, XP004246538, ISSN: 0925-4005.

Osamu Suzuki et al.: "POF-Type Optic Humidity Sensor and Its Application" Technical Digest of the Optical Fiber Sensors Conference OFS 2002, May 6-10, 2002, Portland, OR, USA May 6, 2002 pp. 447-450 XP002513104.

* cited by examiner

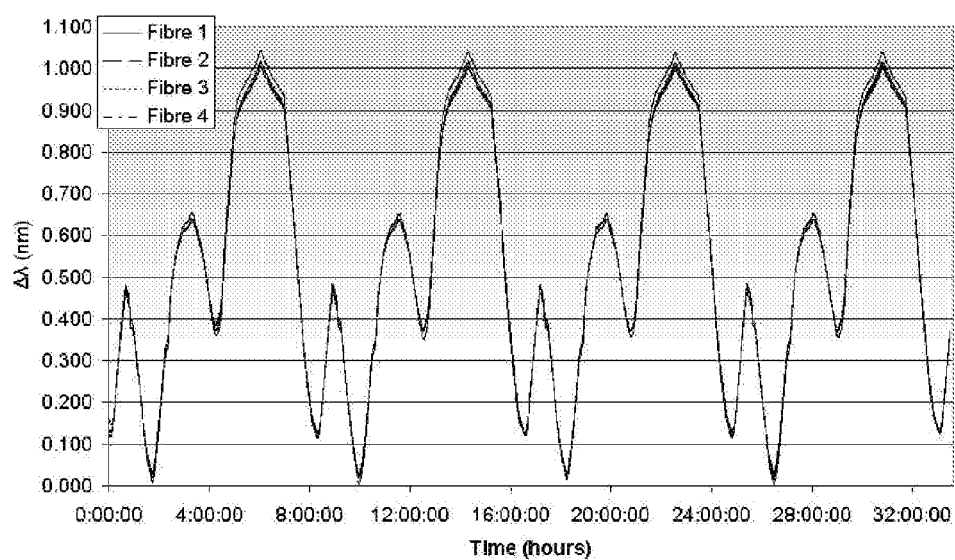
Reproducibility of the manufacturing process and the sensor response for four fibres and four cycli

US 8,831,388 B2

COATED WAVEGUIDE FOR OPTICAL DETECTION

CROSS-REFERENCE TO RELATED APPLICATIONS

This application is a 371 of PPCT/NL2008/050823 filed Dec. 19, 2008, which claims the benefit of European Patent Application No. 07150214.0 filed Dec. 20, 2007, the contents of each of which are incorporated herein by reference.

FIELD OF THE INVENTION

Background of the Invention

The invention relates to a waveguide comprising a grating, to an optical sensor comprising the waveguide and to the use of the sensor for measuring an environmental effect.

Optical sensors have a number of advantages over electronic measuring systems. Optical sensors are for example more reliable in environments that are difficult to access and/or hazardous to humans, environments such as those found in the oil and gas industry, and are usually not adversely affected by the electromagnetic radiation that is generally produced in for example power cable systems, induction furnaces or equipment for nuclear magnetic resonance measurements, such as MRI or NMR equipment. Other advantages are the easy operation of optical sensors on large distances, their small size, their flexibility and/or the possibility to make a sensor system consisting of an array of discrete sensors that all may be read separately from a single optical fibre.

Typical sensor systems that are based on waveguide grating are, e.g., described in detail in U.S. Pat. No. 5,380,995, U.S. Pat. No. 5,402,231, U.S. Pat. No. 5,592,965, U.S. Pat. No. 5,841,131, U.S. Pat. No. 6,144,026, US 2005/0105841, U.S. Pat. No. 7,038,190, US 2003/156287.

One principle on which such sensor systems may be based is an axial strain of the waveguide, as a result of an environmental effect that is to be detected, for example by using a coating on the waveguide that deforms under the influence of the environmental effect. When a waveguide grating, guiding a specific spectrum of light, stretches or shrinks under such axial strain, the spectral pattern of transmitted light and/or the spectral pattern of reflected light (i.e. the spectral response) changes. Such changes in the spectral response provide—when measured—quantitative information on the environmental effect.

US application 2005/0105841 relates to the use of a polyethyleneimine (PEI) monolayer coating on a Long Period Grating waveguide. The coating swells under the uptake of water, which makes a sensor comprising such coating suitable for measuring relative humidity (RH), based on changes of the refractive index of the coating. However, changes in refractive index are not selective for the detection of water, which makes the sensor sensitive to environmental pollutions. The preparation of the sensor is cumbersome due to the slow deposition of the monolayer. Also, the response time is relatively long, especially at a high humidity, and it appears that very high humidities cannot be measured, which results in a small dynamic range of the sensor. The refractive index of the coating should be tuned to the specific waveguide grating and therefore cannot be generally used on other waveguides. Thus, the technology of refractive index sensors is mainly limited to Long Period Grating waveguides, and such waveguides cannot be used in long multiple sensor waveguides.

A thesis by J. L. Elster ("Long Period Grating-based pH sensors for corrosion monitoring, Blacksburg, Va., 1999") relates to a poly-acrylic acid coating on a Long Period Grating waveguide, which was applied to constitute a pH sensor. Such pH sensors are based on a change in refractive index of the coating around the cladding due to changes in the $H^+$-concentration. Such sensors have disadvantages similar to those of the relative humidity sensor described US application 2005/0105841.

U.S. Pat. No. 7,038,190 relates to an optical humidity sensor making use of medical grade polyurethane foam or polyimide to sense humidity. Amongst others, the application describes to provide a fibre with an epoxy acrylate, that has a similar thermal response to polyimide but is relatively insensitive to humidity. Thus, in combination with polyimide it can be used as a fibre grating filter, to correct changes in signal of the grating coated with polyimide due to changes in temperature. Due to the thickness of the polymer layers, the response time is long (hours). No information is given concerning the preparation and the specific properties of the sensors.

Xiamomei Liu et al. (Sensors and Actuators B 96 2003, 468-472) describe a Fibre Bragg grating-based sensor with a polyacrylamide hydrogel coating. A swollen hydrogel shrinks upon contact with an NaCl solution, thus the sensor is proposed to be used to directly determine the NaCl concentration. The coating being a hydrogel, makes the sensor's susceptible to being damaged, as a polyacryl amide hydrogel has a relatively low stiffness. Furthermore, this sensor contains a thick hydrogel layer that cannot be used in thin tubings.

SUMMARY AND DESCRIPTION OF THE INVENTION

It is an object of the present invention to provide a new waveguide comprising a grating which waveguide can be used in an optical sensor, in particular a sensor making use of Bragg reflection or long period grating based detection mechanism, that can serve as an alternative to known waveguide gratings, in particular for measuring moisture, or to measure another analyte or another (change in an) environmental condition, such as (a change in) a physical parameter. It is in particular an object of the invention to provide a novel waveguide that is improved, in particular in that a detection system comprising the waveguide is improved in that it offers at least one of the following advantages: a higher selectivity towards a specific environmental effect, a larger dynamic range, a higher accuracy, a higher robustness, a lower detection limit, a higher sensitivity, a higher reproducibility in terms of repeated measurements with a single waveguide, and a higher manufacturing reproducibility (i.e. results from different waveguides, in particular originating from different batches of manufacturing being increased).

The selectivity of a detection system for measuring a certain environmental condition is the extent to which the detector specifically reacts to a change in a selected environmental conditions, without being affected by a change in other conditions.

The dynamic range of a sensor system is the range of a changeable quantity that can be measured with that sensor system, the limits of which range are defined by the smallest and the largest value of the changeable quantity that can be measured with that sensor system.

The accuracy of a detection system is the closeness of a reading or indication of that detection system to the actual value of the quantity being measured.

Robustness is the extent to which a detection system is resistant to changes in the detection system, influences from a specific sample and influences from the environment other than the condition, other than the changes in the condition to be measured. Accordingly, as a system is more stable, the back ground noise will be less and/or fewer artefacts will occur in the measuring signal, such a spikes, base line drift and/or base line shifts.

The detection limit is the lowest measurable change in a environmental condition. It is determined by the signal to noise ratio. In general, the detection limit for a particular substance is set at a signal to noise ratio of 2 (if the noise is represented as peak to peak) or 4 (if the noise is represented as the root of the mean square noise (RMS noise)). Sensitivity of a detection system is the extent to which the measured signal changes upon a particular change in the concentration or amount of the substance to be detected.

The sensitivity of a detection system is the smallest change in a environmental condition, such as a physical or chemical parameter, that can be detected by the detection system.

BRIEF DESCRIPTION OF THE FIGURE

FIG. 1 is a Reproducibility of the manufacturing process and the sensor response for four fibers and four cycli.

It has now been found that one or more of these objects are realised by providing a waveguide having a coating which comprises a polymer having specific moieties on the chain.

Accordingly, the present invention relates to a waveguide, comprising a grating in at least a part of the waveguide, which waveguide comprises a coating, the coating comprising a polymer, which polymer comprises an aliphatic chain, which aliphatic chain is provided with functional side-chains. The coating preferably is a coating capable of interacting with a chemical substance which presence is to be detected (an analyte), by which interaction the axial strain of the waveguide changes.

In particular, the present invention is directed to a waveguide, comprising a grating in at least a part of the waveguide, which waveguide comprises a coating, the coating comprising a polymer, which polymer comprises an aliphatic chain, which aliphatic chain is provided with functional, preferably hydrophilic, side-chains which side-chains comprise at least one moiety selected from the group of heterocycloalkyl moieties.

The term functional as used herein means capable of interacting with an analyte of interest, or capable of providing the polymer with properties that make the polymer sensitive to (a change in) an environmental condition. Preferably, a functional side-chain is a hydrophilic side-chain.

A side-chain may be adapted to the specific application, e.g. for improved selectivity towards measurement of a specific analyte or of (a change in) a specific physical parameter.

For the purpose of the invention, the term waveguide is used for optical waveguides. An optical waveguide is a physical structure that guides electromagnetic waves in at least part of the optical spectrum, i.e. in at least part of the spectrum formed by the infrared, visible and ultraviolet ranges of the electromagnetic spectrum. In general, a waveguide is of elongate form. Common types of waveguides include optical fibres, e.g. as referred to in the above cited prior art, and rectangular waveguides. Waveguides are commercially obtainable from various sources. Manufacturing and applications can be found in the Encyclopedia of Laser Physics and Technology (http://www.rp-photonics.com/encyclopedia.html). Fibre Bragg Gratings are supplied by FOS&S, Geel, Belgium.

For the purpose of the invention, hereinafter with "grating" is meant a periodic variation of the refractive index of waveguide material in a segment of a waveguide core. A grating reflects particular wavelengths of electromagnetic waves and transmits other wavelengths, and can be used as an inline optical filter or as a wavelength-specific reflector.

For the purpose of the invention, hereinafter with an aliphatic chain is meant a chain that is free of an aromatic moiety in the chain. Typically, an aliphatic chain comprises single bonds, which contribute to the flexibility of the material.

For the purpose of the invention, with hydrophilic is meant the capacity of a molecular entity or of a substituent to interact with polar solvents, in particular with water, or with other polar groups.

A polar group is any chemical grouping in which the distribution of electrons is uneven, enabling it to take part in an electrostatic interaction, for instance a hydrogen bonding or another dipole-dipole interaction with an analyte of interest.

A side-chain is in particular considered polar in case the polar component of the Hansen solubility parameter is higher than 10, preferably higher than 15.

A side-chain is in particular considered polar in case the surface of the polymer can be wetted with water, forming a water film or coating on the surface. A polar polymer usually has a high surface tension and/or a high dielectric constant.

The dielectric constant of a polymer is in particular considered high if it is at least 8, more in particular at least 10.

The surface tension is in particular considered high if it is at least 35 dynes/cm, more in particular at least 39 dynes/cm.

The present invention further relates to a sensor system comprising a waveguide according to the invention, a light source, and a photo-detector, capable of determining the intensity of the light reaching the detector as a function of the wavelength.

A sensor system according to the invention may in particular be used for the detection of an analyte, more in particular for detecting at least one analyte selected from the group of water, carbon monoxide, oxygen, carbon dioxide, hydrogen cyanide, hydrogen sulfide, ammonia, $H_2S$, metal ions, metal-containing ions, biomolecules (e.g. DNA, RNA, a peptide, an enzyme), $H^+$, and hydroxide ions.

Further, a sensor system according to the invention may be used to measure a physical effect, such as a change in temperature, pressure or voltage.

The coating can be prepared by UV curing instead of thermocuring.

A grating according to the invention may in particular be a Fibre Bragg Grating (FBG) or a Long Period Grating (LPG).

In a specific embodiment, a waveguide according to the invention comprises a multitude of gratings, which are typically spatially apart, preferably 2-500, in particular 2-100 gratings. In particular for a fibre Bragg grating, it is useful to have a multitude of gratings. This allows each grating on the waveguide to be designed in such a way that it creates a spectral response that is unique with respect to the other gratings on the waveguide. This allows, for instance, a single waveguide to be used to measure an environmental effect at a multitude of places. From a change in a specific unique spectral response (measured at one or both of the ends of a waveguide) it will be clear in the vicinity of which grating an environmental effect has changed. In particular in case different gratings are coated with different polymeric materials, adapted to respond towards a change in different environmental effect, this also allows the use of a single waveguide to measure a multitude of environmental effects.

The present invention further relates to an object comprising a waveguide according to the invention, in particular an object selected from the group of infrastructural elements, such as dikes, dams, tunnels, aqueducts, bridges, roads; landfills, subterranean water, oil or gas reservoirs, high voltage power cables, induction furnaces, equipment for nuclear magnetic resonance measurements, such as MRI or NMR equipment, and equipment for (chemical) processing industry, such as reactors, pipelines, separation devices, storage containers, and the like.

A coating according to the invention comprises a polymer, which is a substance of which the molecules, in particular organic molecules, are built up from at least two monomeric units, usually at least 10 monomeric units, preferably at least 50 monomeric units, at least 100 monomeric units, or at least 250 monomeric units. The upper limit is not particularly critical and can be, for instance, 1000, 10 000, 100 000, 1 000 000, or more than a 1 000 000 monomeric units. The monomeric units may be the same (a homopolymer) or the polymer may be composed of two or more different monomers (a copolymer).

The polymer comprises an aliphatic chain of monomeric units, which monomeric units may be of one or more different types. In general, at least one type of monomer contains a moiety that is the side-chain of the polymer or contains a moiety that may be converted into the side-chain of the polymer. Preferred polymers with an aliphatic chain are polymers composed of at least one monomer selected from the group of acryloylmorpholine, acrylic acid, acrylamide, and vinyl pyrrolidone.

Suitable side-chains include moieties selected from the group consisting of heterocycloalkyl moieties, $-R_n-OH$, $-R_n-CN$, $-R_n-NH_2$, $-R_n-NO_2$, $-R_n-COOH$, $-R_n-(CO)(NH_2)-$, $-R_n-(CO)(NHR')-$, $-R_n-(CO)(NR'R'')-$, $-R_n-NHR'$ and $R_n-NR'R''$. In these moieties, each R, R' and R'' independently represents a hydrocarbon moiety, which may be substituted or unsubstituted. The hydrocarbon moiety optionally comprises one or more heteroatoms. In particular, R, R' and/or R'' may comprise 1-20, 1-12 or 1-6 carbons. More in particular, R, R' and/or R'' may comprise a substituted or unsubstituted C1-C4 alkyl. R' and R'' may together form a cyclic structure such as a heterocycloalkyl moiety. The integer n is 1 or 0.

In an embodiment, at least part of the side-chains of a polymer according to the invention comprise functional groups that are Lewis and/or Brønsted acids and/or functional groups that are Lewis and/or Brønsted bases. The use of such acids or bases is particularly suitable for a sensor that measures pH or the presence of water.

Polymers comprising side-chains containing a carboxylic acid moiety or an amine moiety may be used to provide a waveguide for use in a pH sensor, for use in an ammonia sensor, or for use in an acid (e.g. HCl) sensor.

In an embodiment, at least part of the side-chains comprise functional groups that are capable of forming a complex or another bond with an ion, in particular a metal ion or an ionic compound containing a metal ion.

For instance side-chains may comprise a carboxylic acid group, e.g. for detecting an alkaline earth metal ion, such as $Ca^{2+}$ or $Ba^{2+}$.

For instance, side-chains may comprise a crown ether.

In particular for transition metal ions specific ligands are known in the art, e.g. from Dictionary of Inorganic Compounds, Chapman & Hall, London, first edition 1992. Examples of ligands that can be attached to the polymer as (part of) a side-chain are cyclopentadienyl, cyclooctadiene, triamines, diamines, acetonitrile/benzonitrile, salen, porphyrin, triphenyl phosphine, tetramethyldiamine, trimethoxyphosphine, bipyridine, imidazole, terpyridine and phenantroline. The use of such functional groups is particularly suitable for a sensor that measures the presence of one or more types of metal ions as an analyte via their complexation to the specific ligands.

In a preferred embodiment, the side-chains comprise at least one moiety selected from the group of heterocycloalkyl moieties, wherein the heterocycloalkyl moiety comprises at least one heteroatom selected from the group of nitrogen, sulphur and oxygen. Crown ethers are examples of heterocycloalkyl moieties. More preferably, the heterocycloalkyl moiety is selected from the group of morpholine moieties, pyrrolidone moieties, oxazolidine moieties, piperidine moieties, tetrahydrofuran moieties, tetrahydropyran moieties, piperazine moieties and dioxane moieties. Particularly preferred are morpholine moieties and pyrrolidone moieties. The use of such functional groups is particularly suitable for a sensor that can be used to measure the presence of water.

A polymer according to the invention may comprise crosslinks. A typical crosslinking degree is 1 to 50 crosslinks per 100 monomer units. The polymeric chains may be crosslinked reacting the polymer with a crosslinker, for example 1 to 30 w % of crosslinker, based on the total weight of the polymer before crosslinking.

Preferred examples of crosslinkers are polyfunctional epoxides and polyfunctional peroxides or radical forming moieties, epichlorohydrine.

It is also possible to prepare a crosslinked polymer by polymerising a monomer mixture comprising at least one monomer for forming the aliphatic chain and at least one multifunctional monomer for forming the crosslinks. The concentration of multifunctional monomer, may for instance by chosen in the range of 1 to 30 w % based on total monomers. Preferred examples of crosslinkers are polyfunctional aromatic urethane (meth)acrylates and polyfunctional alkylene glycol (meth)acrylates and aliphatic di(meth)acrylates.

The swellability properties are a function of the degree of crosslinking. Accordingly, the degree of crosslinking may be used to optimise the coating for a certain application. For example, for a humidity sensor, a relatively low crosslinking degree may be desired, e.g. in the range of 1 to 20 crosslinks per 100 monomeric units. For example, for a pH sensor a relatively high crosslinking degree may be desired, e.g. in the range of 20 to 50 crosslinks per 100 monomeric units. In general, a higher crosslinking degree tends to lead to a lower swelling degree of the coating, in response to a specific change in the environmental effect to be measured.

Preferred crosslinked polymers with an aliphatic chain are crosslinked poly(acryloylmorpholine), crosslinked poly(acrylic acid), crosslinked poly(acrylamide), crosslinked poly(vinyl pyrrolidone) and crosslinked copolymers thereof. Particularly preferred crosslinked polymers are copolymers of the said crosslinked polymers crosslinked with at least one crosslinker, such as at least one crosslinker selected from polyfunctional aromatic urethane acrylates and polyfunctional ethylene glycol (meth)acrylates.

A coating layer according to the invention usually has a thickness of at least 0.5 μm, preferably of 10 μm, more preferably of at least 20 μm. Usually, the thickness is 200 μm or less, in particular, at most 100 μm, preferably 75 μm or less, more preferably 50 μm or less. A relatively thin layer is advantageous for a short response time, a relatively thick layer is advantageous for a high sensitivity.

The coating is usually non-gellated, in particular not gellated with water, although in principle in a specific embodiment a specific coating may form a gel during its use in a sensor, especially as a result of an absorption of certain analytes into the coating. A gelled coating may be more susceptible to damage due to mechanical forces (e.g. rubbing against a surface, erosion-like effect due to fluid flowing against the coating, bending of the waveguide). Instead of a (hydro)gel, the coating of the waveguide may be an amorphous, crystalline, or semi-crystalline solid (at 25° C.). The coating is usually essentially water-free (unless water is a compound to be analysed, in which case the coating of a waveguide in a sensor of the invention in general absorbs water to be detected). If present, the water content usually is 0-10 wt. %, based on the total weight of the coating, in particular 5 wt. % or less, more in particular 2 wt. % or less. A relatively low water content is amongst others considered advantageous for providing a coating that has a good resistance against damage due to mechanical forces. Further, a relatively low water content is considered advantageous for a high mechanical strength/stiffness, especially at elevated temperatures.

The invention further relates to a method for preparing a waveguide according to the invention, comprising providing a waveguide, preferably pretreating the waveguide with a silane solution (to improve wetting and adhesion)

applying a coating composition comprising the polymer or a precursor thereof to at least part of the surface of the waveguide, whereby the coating composition forms a layer at least substantially surrounding a grating of the waveguide, and curing the coating composition.

In an advantageous method of the invention, the waveguide or at least a part thereof to be coated is placed in a mould, leaving a space between the outer surface of the waveguide or part thereof inside the mould and the inner surface of the mould, introducing the coating composition into the space; and curing the coating composition. Such method is especially advantageous in that it allows the manufacture of a plurality of waveguides, which when used in a sensor system of the invention show a good manufacturing reproducibility.

It is possible to coat a selected part of the waveguide. Such part is not limited to an extremity of the waveguide. One or more parts remote from the extremities can be selectively coated.

In a highly preferred method, the mould is transmittant for radiation used for initiating the polymerization. In particular, the mould may be transparent to light of a wavelength suitable to activate the polymerisation (usually UV-light or light in the visible range), and wherein the coating composition is cured inside the mould using light to activate the polymerization. Usually, in such case the composition used for preparing the coating comprises a photo-initiator. The light used is selected such that it is capable of activating the initiator. Suitable photo-initiators and suitable wavelengths for activation are generally known in the art.

EXAMPLES

Examples of suitable free-radical photoinitiators include benzoin derivatives, methylolbenzoin and 4-benzoyl-1,3-dioxolane derivatives, benzilketals, α,α-dialkoxyacetophenones, α-hydroxy alkylphenones, α-aminoalkylphenones, acylphosphine oxides, bisacylphosphine oxides, acylphosphine sulphides, halogenated acetophenone derivatives, and the like.

Other examples of suitable initiators include benzophenone, hydroxymethylphenylpropanone, dimethoxyphenylacetophenone, 2-methyl-1-[4-(methylthio)-phenyl]-2-morpholino-propan-1-one, 1-(4-isopropylphenyl)-2-hydroxy-2-methylpropan-1-one, 1-(4-dodecyl-phenyl)-2-hydroxy-2-methylpropan-1-one, diethoxyphenyl acetophenone, and the like. Phosphine oxide photoinitator types (e.g., Darocur TPO by Ciba) such as benzoyl diaryl phosphine oxide photoinitiators may be used.

The invention will now be illustrated by the following examples.

Example 1

General

Several polymers were evaluated for their ability to swell when exposed to water vapour. In Table 1 and 2, these polymers are listed, together with the formulation that was used. The swelling ratio and the capability of exercising a stress to the glass fibre was measured by applying the coating to a metal strip, drying the coating at 50° C. and exposing the strip to several relative humidities. When the polymer coating is taking up water vapour, the coatings swells and the strip is bend. The degree of bending is a measure for the internal stress in the coating and for the ability to strain a glass fibre.

TABLE 1

Vinyl polymers

| Polymer | Solvent | Concentration (w %) | Degree of swelling (w %) at 90% RH |
|---|---|---|---|
| Polyvinylpyrrolidone | Ethanol | 50 | 50 |
| Polyvinylalcohol | Water | 10 | 60 |
| Polyacryloylmorpholine | Water | 10 | 25 |
| Polyacrylic acid | Water | 25 | 50 |
| Sodium Polyacrylate | Water | 1 | 200 |

TABLE 2

Other relevant polymers

| Polymer | Solvent | Concentration (w %) | Degree of swelling (w %) at 90% RH |
|---|---|---|---|
| Hydroxypropylcellulose | 10% NaOH in $H_2O$ | 5 | 145 |
| Starch | Water | 10 | 130 |
| Gelatin | Water | 5 | 60 |
| Ac-Di-Sol | Water | 1 | 250 |

Example 2

3.0 g polyvinylpyrrolidone (PVP) K30 (water responsive polymer) was dissolved in 3.0 g ethanol at 50° C. To this solution 3.7 g water was added and 0.3 g 4,4'-diazidostilbene-2-2'-disulphonic acid disodium salt (crosslinker) was added and dissolved. 5.5 g of this solution was further diluted with 4.5 g ethanol. An acrylic coated Fibre Bragg Grating (FBG) glass fibre was stripped of the acrylic coating. The stripped fibre was dipped in the PVP solution using a dipcoater to generate a uniform coating and cured under UV light at RT and ambient RH. A coating layer of ca 1 μm was deposited on the fibre. This dipping procedure was repeated 20 and 50 times and a coating of 20 and 50 μm was obtained after curing and drying. The dipping experiment was also repeated after pretreatment of the glass fibre with methacryloyl silane in order to improve the adhesion of the coating to the glass.

Example 3

3.0 g acryloylmorpholine (for preparing a water responsive polymer) was mixed with 1.0 g Actilane 170 (crosslinker) and 0.2 g Darocure 1173 (photoinitiator). The stripped fibre from example 2 was dipped in the mixture and cured under UV light at RT and ambient RH. After dipping the surface of the fibre developed a bead-string shape. This surface irregularity was reduced by reducing the viscosity of the mixture by adding a solvent. Better results were obtained by using a mould in which the coating was moulded around the stripped fibre. A polymer mould, transparent for UV light was placed around the fibre. The coating composition was injected into the mould and the mould was placed in the UV cube for curing. The resulting coating did not stick to the polymer mould. A thick smooth coating was obtained. The change of the maximum in reflected wavelength between 50 and 90% RH was 0.1 nm.

Example 4

7.1 g acryloylmorpholine (for preparing a water responsive polymer) was mixed with 2.4 g Actilane 170 (crosslinker), 2.0 g triethylene glycol dimethacrylate (crosslinker) and 0.5 g Darocure 1173 (photoinitiator). A long fibre bragg grating was stripped for 2 cm's at the position of the grating. A polymer mould, transparent for UV light was placed around the fibre. The coating composition was injected into the mould and the mould was placed in the UV cube for curing. The resulting coating did not stick to the polymer mould. A thick smooth coating was obtained. The change of the maximum in reflected wavelength between 50 and 90% RH was 0.2 nm.

Example 5

5.5 g acryloylmorpholine (for preparing a water responsive polymer) was mixed with 1.8 g Actilane 170 (crosslinker), 9.9 g triethylene glycol dimethacrylate (crosslinker), 2.3 g acrylamide and 0.25 g Darocure 1173 (photoinitiator). Four fibre bragg gratings were stripped for 2 cm's at the position of the grating. The fibres were introduced in a Vytran PTR-200 recoater and the monomer mixture was injected into the 260 µm mould and UV cured. The resulting coating did not stick to the glass mould. The four fibres were submitted to several relative humidity-temperature cycli. RH ranged from 45 to 100% and the temperature from 20 to 85° C. FIG. 1 shows the reproducibility of the manufacturing process and the sensor response. The first peak is measured at 23° C. with RH starting at 50%, increasing to 100% and decreasing to 50%, then the temperature is raised to 50° C. and the same RH cycle is performed. Then, the temperature is increased again to 85° C. followed by a new RH cycle. This is repeated four times. The results show that each fibre has the same response to an increase in both temperature and relative humidity for at least four consecutive cycles.

The invention claimed is:

1. A waveguide, comprising: a grating in at least a part of the waveguide, which waveguide further comprises a coating, the coating comprising a polymer, which polymer comprises an aliphatic chain, which aliphatic chain is provided with functional, hydrophilic, side-chains comprising at least one moiety selected from the group of heterocycloalkyl moieties,
   wherein the coating is capable of interacting with a chemical substance which presence is to be detected; and
   wherein the interaction causes an axial strain of the waveguide to change.

2. The waveguide according to claim 1, wherein the heterocycloalkyl moiety comprises at least one heteroatom selected from the group of nitrogen, sulphur and oxygen.

3. The waveguide according to claim 2, wherein the polymer contains side-chains comprising at least one heterocycloalkyl moiety selected from the group of morpholine moieties, pyrrolidone moieties, pyrrolidine moieties, oxazolidine moieties, piperidine moieties, tetrahydrofuran moieties, tetrahydropyran moieties, piperazine moieties and dioxane moieties.

4. The waveguide according to claim 1, wherein the coating is an amorphous solid, a crystalline solid or a semi-crystalline solid.

5. The waveguide according to claim 1, wherein the grating of the waveguide comprises a fiber bragg grating and/or a long period grating.

6. The waveguide according to claim 1, wherein the coating layer on the waveguide has a thickness of 0.5 µm to 200 µm.

7. The waveguide according to claim 1, wherein the polymer comprises cross-links.

8. The waveguide according to claim 1, wherein the polymer contains side-chains comprising acidic functional groups and/or basic functional groups.

9. The waveguide according to claim 1, wherein the polymer contains side-chains comprise functional groups that are capable of forming a complex with an ion.

10. The waveguide according to claim 1, wherein the grating is a fiber bragg grating, and the waveguide comprises a plurality of gratings that are spatially apart, preferably 2-100 gratings that are spatially apart.

11. The waveguide according to claim 1, wherein the coating comprises 0-10 wt. % water, based on the total weight of the coating.

12. A sensor system comprising the waveguide according to claim 1, a light source, and a photo-detector.

13. An object comprising a waveguide according to claim 1, the object being selected from the group of infrastructural elements, including dikes, dams, tunnels, aqueducts, bridges, roads; landfills, subterranean water, oil or gas reservoirs, high voltage power cables, induction furnaces, equipment for nuclear magnetic resonance measurements, including MRI or NMR equipment, and equipment for processing industry, including reactors, pipelines, separation devices, storage containers, and the like.

14. The waveguide according to claim 1, wherein the coating layer on the waveguide has a thickness of 10 µm to 100 µm.

15. The waveguide according to claim 1, wherein the coating layer on the waveguide has a thickness of 20 µm to 50 µm.

16. The waveguide according to claim 1, wherein the polymer contains side-chains comprise functional groups that are capable of forming a complex with a metal ion or ionic compound containing a metal ion.

17. The waveguide according to claim 1, wherein the polymer contains side-chains comprise functional groups that are capable of forming a complex with a metal ion selected from the group of Ca, Mg, Sr, Ba, Zn, Hg, Fe and Mn.

18. The waveguide according to claim 1, wherein the coating comprises 5 wt. % of water or less, based on the total weight of the coating.

19. The waveguide according to claim 1, wherein the coating comprises 2 wt. % of water or less, based on the total weight of the coating.

20. The waveguide according to claim 1, wherein the grating is present in a waveguide core, and the coating is provided on said waveguide core.

21. The waveguide according to claim 1, wherein the polymer is an organic polymer.

22. The waveguide according to claim 21, wherein the organic polymer is selected from the group consisting of crosslinked poly(acryloylmorpholine), crosslinked poly(acrylic acid), crosslinked poly(acrylamide), crosslinked poly(vinyl pyrrolidone) and crosslinked copolymers thereof.

23. The waveguide according to claim 1, wherein the polymer is water-swellable.

\* \* \* \* \*